US010786181B1

(12) United States Patent
Echols

(10) Patent No.: US 10,786,181 B1
(45) Date of Patent: Sep. 29, 2020

(54) GONIOMETER

(71) Applicant: John D Echols, Key West, FL (US)

(72) Inventor: John D Echols, Key West, FL (US)

( * ) Notice: Subject to any disclaimer, the term of this patent is extended or adjusted under 35 U.S.C. 154(b) by 0 days.

(21) Appl. No.: 16/519,793

(22) Filed: Jul. 23, 2019

(51) Int. Cl.
*A61B 5/11* (2006.01)
*A61B 5/00* (2006.01)
*A61B 5/107* (2006.01)

(52) U.S. Cl.
CPC .......... *A61B 5/1122* (2013.01); *A61B 5/0022* (2013.01); *A61B 5/1071* (2013.01); *A61B 5/742* (2013.01)

(58) Field of Classification Search
CPC ..... A61B 5/1122; A61B 5/742; A61B 5/1071; A61B 1/0022; A61B 5/0022
USPC ........................................................ 600/595
See application file for complete search history.

(56) References Cited

U.S. PATENT DOCUMENTS

| | | | | |
|---|---|---|---|---|
| 4,436,099 A | * | 3/1984 | Raftopoulos | A61B 5/1071 600/587 |
| 4,442,606 A | * | 4/1984 | Graham | G01B 3/56 33/1 N |
| 4,711,242 A | | 12/1987 | Petrofsky | |
| 4,834,057 A | | 5/1989 | McLeod | |
| 5,792,077 A | | 8/1998 | Gomes | |
| 5,826,578 A | | 10/1998 | Curchod | |
| 6,447,425 B1 | * | 9/2002 | Keller | A61B 5/1071 482/8 |
| 7,668,588 B2 | * | 2/2010 | Kovacs | A61B 5/0404 600/509 |
| 8,012,107 B2 | | 9/2011 | Einav | |
| 8,607,465 B1 | | 12/2013 | Edwards | |
| 2002/0143279 A1 | | 10/2002 | Porier | |
| 2008/0161731 A1 | | 7/2008 | Woods | |
| 2008/0221485 A1 | * | 9/2008 | Lissek | A61B 5/103 600/595 |
| 2009/0038168 A1 | | 2/2009 | Wixey | |
| 2010/0043243 A1 | | 2/2010 | Li | |
| 2015/0101206 A1 | | 4/2015 | Smith | |

* cited by examiner

*Primary Examiner* — Daniel L Cerioni
(74) *Attorney, Agent, or Firm* — Christopher J. Van Dam; Chris Vandam

(57) ABSTRACT

A device and method for measuring the angle and range of motion of a body joint used in the course of medical treatment. Index marks are placed on the limbs of the patient that correspond to registration indicators on the arms of the device. This allows consistent application of the device in measurement sessions over time to ensure consistent measurements of the joint. A fixed display and a wireless broadcast of the angle are for reading the angles of the joint.

3 Claims, 4 Drawing Sheets

GONIOMETER

BACKGROUND OF THE INVENTION

1. Field of the Invention

The present invention relates to human medical treatment devices and methods, and more particularly, to an improved way of precisely measuring the range of articulation of a human leg or arm joint.

2. Description of the Related Art

Several designs for goniometers and methods of measuring human joint articulation range have been designed in the past. None of them, however, includes a precision instrument that has a digital readout with wireless device integration and that registration notches that align with healthcare provider applied index marks on the joint to allow for consistent and repeatable measurement of joint articulation range over a period of time of medical treatment that does not require the patient to continually wear the device but can be applied at periodic treatment sessions.

Applicant believes that the closest reference corresponds to U.S. Pat. No. 5,792,077 issued to Gomes. However, it differs from the present invention because the present device provides an indexing notch on each end of the arms of the device so that measurements in treatments separated in time are able to accurately repeat the range of joint motion to a far greater degree that Gomes. Further, the present device provides for an improved display to allow the healthcare provided to observe the range of motion measured on the device from in front of the patient while assisting the patient in the rehabilitation treatment. Further, the present device includes the ability to wirelessly transmit the angles of the joint and relative angles of the limbs being measured in real time to aid in determining the course of treatment while allowing the therapist or other healthcare provided to provide manual safety bracing and two-handed support to the patient.

Other patents describing the closest subject matter provide for a number of more or less complicated features that fail to solve the problem in an efficient and economical way. None of these patents suggest the novel features of the present invention.

A brief abstract of the technical disclosure in the specification and title are provided as well for the purposes of complying with 37 CFR 1.72 and are not intended to be used for interpreting or limiting the scope of the claims.

Without limiting the scope of the invention, a brief summary of some of the claimed embodiments of the invention is set forth below. Additional details of the summarized embodiments of the invention and/or additional embodiments of the invention may be found in the detailed description of the invention below.

SUMMARY OF THE INVENTION

It is one of the main objects of the present invention to provide a joint measurement device and method of use that is able to measure joint range, be removed from the patient and later be re-attached to the patient and provide precisely consistent placement on the limbs on either side of the joint being measured.

It is another object of this invention to provide a joint goniometer that is easy for the healthcare provided to view the joint angle hands free so that full attention and both hands can be used to assist the patient during physical therapy and diagnosis.

It is still another object of the present invention to provide a device and method that improves the safety of the patient and reduce pain during treatment and evaluation because the healthcare provided can assist with joint movement.

It is yet another object of this invention to provide such a device and method of joint range testing that is inexpensive to manufacture and maintain while retaining its effectiveness.

Further objects of the invention will be brought out in the following part of the specification, wherein detailed description is for the purpose of fully disclosing the invention without placing limitations thereon.

These and other embodiments which characterize the invention are pointed out with particularity in the claims annexed hereto and forming a part hereof. However, for a better understanding of the invention, its advantages and objectives obtained by its use, reference can be made to the drawings which form a further part hereof and the accompanying descriptive matter, in which there are illustrated and described various embodiments of the invention.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
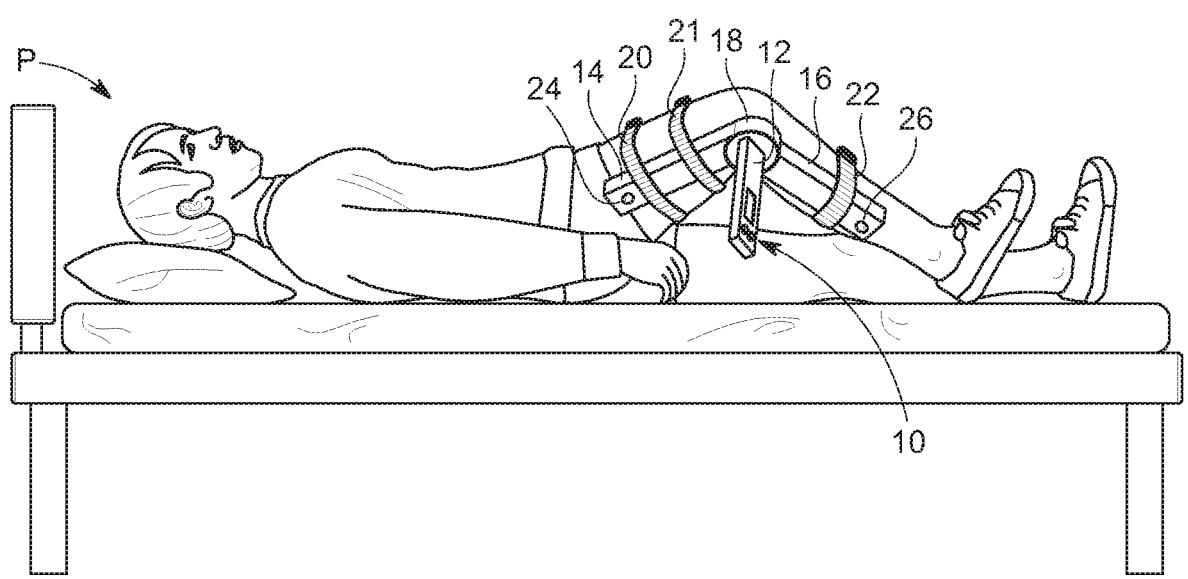
FIG. 1 shows a perspective view of a patient wearing a goniometer during measurement of a knee joint.

While this invention may be embodied in many different forms, there are described in detail herein specific embodiments of the invention. This description is an exemplary of the principles of the invention and is not intended to limit the invention to the particular embodiments illustrated and described.

For the purpose of this disclosure, like reference numerals in the figures shall refer to like features unless otherwise indicated or is obvious by context.

The subject device and method of use is sometimes referred to as the device, the invention, the goniometer, the joint measuring device, the joint protractor, the machine or other similar terms. These terms may be used interchangeably as context requires and from use the intent becomes apparent. The masculine can sometimes refer to the feminine and neuter and vice versa. The plural may include the singular and singular the plural as appropriate from a fair and reasonable interpretation in the situation. The term goniometer is intended to include generally the class of device that aids in measuring angles between parts or pieces of any type or classification.

In a medical treatment setting it may be desirable for the treating healthcare provided to take a precise measurement of the range of motion of a joint between segments of a patient in treatment. It is important for the provider to be able to accurately measure the range of motion of a joint. It is further critical to be able to consistently, over a series of measurements spread out over time, to compare relative range of motion of that specific joint in that specific patient.

For example, if on one treatment session a particular measurement was taken to determine a joint range of articulation, it is important that the measuring device (goniometer) be consistent relative to the two adjoining bones that for the joint being measured. If the measuring device is not consistently placed against the body in a repeatable manner then the comparative measurements are not as accurate as would be needed for proper analysis of the joint.

Prior art has complicated methods of clamping parts of the measuring instrument onto the body of the patient with only marginally consistent results. These devices also do not fit all body types and sizes. Further, when different healthcare providers use the device, possibly with varying skill and experience levels, the consistency of the measurements is not assured.

Without consistent and accurate joint range of movement measurements taken of the course of a treatment the future course of treatment cannot be most effectively determined. For example, during physical rehabilitation after an injury or illness it is important to know the rate of joint range improvement or degradation over a series of treatments spread out over days, weeks or months.

Referring now to the drawings, where the present invention is generally referred to with numeral 10, it can be observed that it basically includes a beam 12, an arm 14, an arm 16, a hinge 18, a strap 20, a strap 21, a strap 22, a notch 24, a notch 26, a display 28, controls 30, a closure 32, a closure 33, a closure 34, a mark 36, a mark 38, a signal 46 and a device 48.

For contextual details it may be further observed that the device and process may be applied to, for example, a patient "P", a joint 40, a leg 42 and a leg 44. It should be appreciated that other joints may also be measured, such as an elbow between an upper arm and lower arm. Similarly, the device may be applied to limbs of animals with a similar application of device and method of use.

FIG. 1 shows a patient P lying in a bed as might be typical during use of the device for measuring the range of motion of a human knee joint. The patient P could equally be on another type of seating arrangement, standing or laying down. The position of the patient is not critical to the use of the goniometer device. The use of the device independent of the position of the patient P and can therefore be used in a wide variety of clinical settings.

Figure 2:
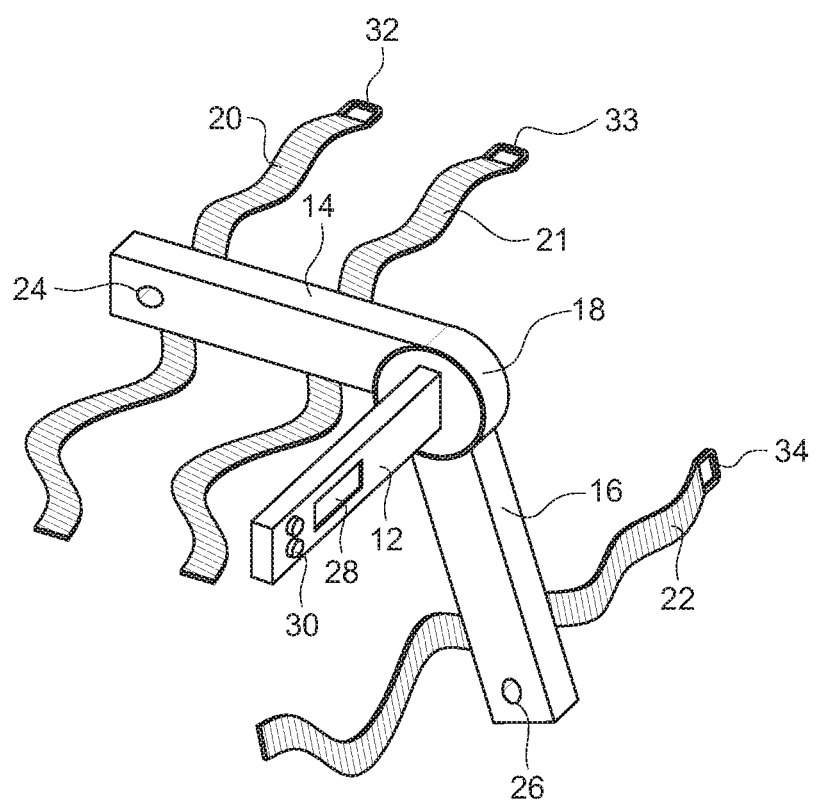
FIG. 2 shows a perspective view of a goniometer unattached from a patient.

The goniometer is shown isolated from the patient P in FIG. 2 and applied to a patient P in FIG. 1 for context. The arm 14 is temporarily affixed to the upper leg 42 with straps 20 and 21. The straps 20 and 21 include closures 32 and 33 so that the straps 20 and 21 can be comfortably fitted to the leg 42. The closures 32 and 33 allow for easy installation and removal of the arm 14 from the patient's P leg by a practitioner of any skill level.

Similarly, the strap 22 affixes the arm 16 of the device to the lower leg 44 of the patient. The closure 34 allows ready adjustment, application and removal of the arm 16 from the patient by one of almost any skill or experience level.

A notable feature on the device is the display 28 integrated into the beam 12 connected to the device on or near the hinge 18. The display 28 shows in a readable format the actual angle between the arm 14 and the arm 16 in near real time. The display 28 could also be equally mountable on either the arm 14 or 16 in a horizontal or vertical orientation so as to be visible to the operator or the patient P.

The display 28 shows the angle between the arms 14 and 16 about the hinge 18 derived electronically from hardware and sensors commercially available and used in a variety of measuring equipment. The display 28 electronically connects to the angle measuring hardware to display the angle between the arms 14 and 16. The angle determining mechanism and the display are generally battery powered.

Generally, the electronic circuits that control the display 28 and the angle measuring mechanism are housed within the hinge 18 housing and/or the beam 12. This protects the mechanisms and also provides a suitable mounting structure to maintain the several elements of the device in a compact form factor.

A control 30 may be provided to calibrate or zero the angle displayed prior to use. A control 30 may also be provided to turn the electronic circuits in the angle sensing mechanism and to preserve battery power. The battery may be replaceable as needed to ensure adequate power supply to power the angle sensing mechanism as well as the display and wireless broadcasting of the measurements.

The precise point where the display 28 is located is not critical as long as the display is readable by either or both the patient P and the technician assisting in using the goniometer during use.

By being able to see the display 28 the operator and/or patient may be able to use both hands (or other not measure limbs) during the testing process. For example, if a knee joint is being measures the hands may be free to stabilize the patient P or could help the patient P move the leg if it is difficult or painful for the patient P to do so using the muscular structure of the leg being tested.

Figure 4:
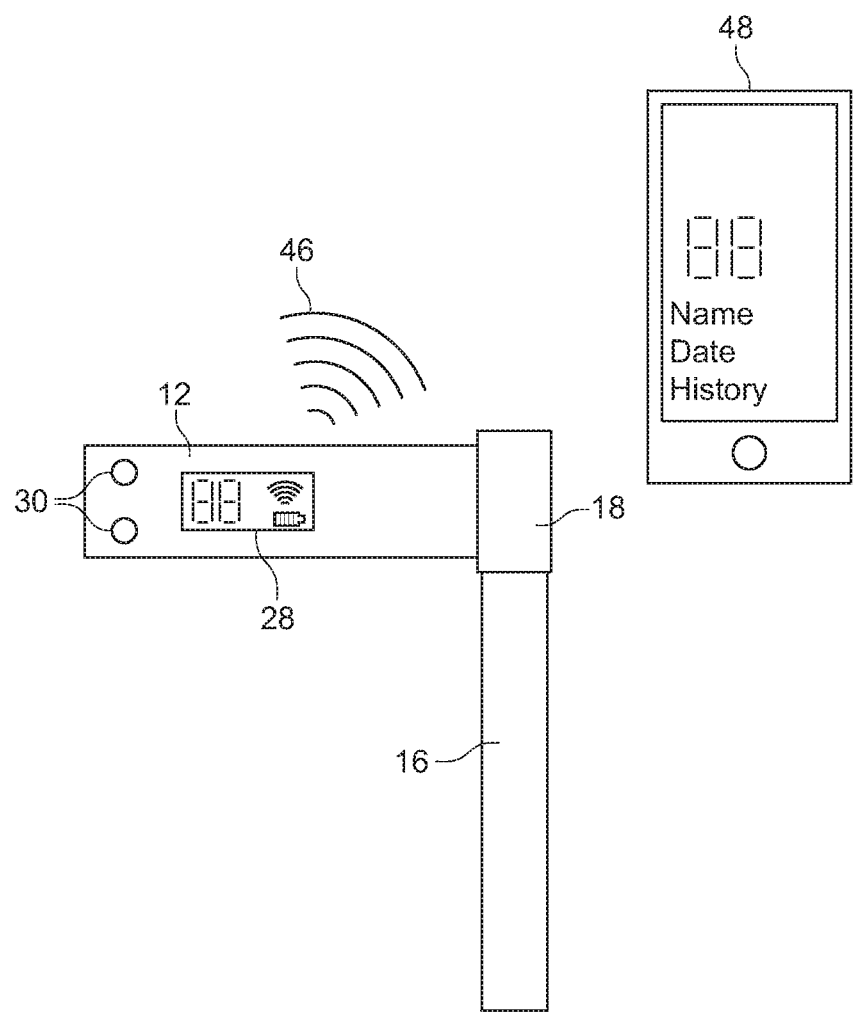
FIG. 4 shows an elevation view of a goniometer in relation to an example of a device receiving the measurement data wirelessly.

FIG. 4 demonstrates a wireless broadcast feature of the device. A signal 46 can be broadcast from the device to a remote device 48. The remote device 48 can display the angle of the goniometer similar to the value shown on the display 28 fixed on the device itself. The device 48 can then record the metrics of the range of motion test, for example including the degrees of movement measured, the name of the patient P, the date of the test and any other relevant information to the process.

The device 48 may also have other software to facility the ease of use of the goniometer. The display on the device 48 may be in addition to or in substitution for the display 28 on the goniometer beam 12 (or other location on the device). The display 28 may optionally show the status or strength of the wireless broadcast signal 46 or the status of the battery reserve in the device.

The wireless signal generally is a short range broadcast such as Bluetooth®, WiFi, cellular network or any other known means to be able to send data from a device such as the goniometer to another computing device located nearby, for example within a hundred meters or so. Longer range signaling would also be equally effective if necessary depending on the circumstances.

Having the angles delivered to a remote computing device over the internet over long distances are also contemplated to be within the inventive scope of the device. In this way a patient P may be able to test themselves at home and have the angle data sent to their healthcare provider at a distance of many miles.

The device 46 may be a hand held personal computing device, like a phone, or could be a proprietary remote reader that primarily works with the goniometer. Alternatively, the remote device 46 could be a general purpose computing device that is used for other things in the clinical setting.

The device 48 may also be provided to, for example, a doctor who is monitoring the measurement session while a physical therapist is actually helping the patient manipulate the joint 40. In this way both the therapist and the doctor can be involved with the data in real time as the information is gathered.

It is important for consistently measuring the joint 40 movement that the arm 14 and arm 16 be connected to the respective leg 42 and leg 44 so that they move together when the patient P articulates the joint 40. If there is play or slop in the connection between the device and the patient P then there may not be consistent measurement.

The closures 32, 33 and 34 may be any type of commonly available means to connect parts of the strap 20, 21 or strap 22 onto itself or the respective arm 14 or arm 16 to effectively connect the device to the body of the patient P. For example, the closures 32 and 34 could be a hook and loop fastener system, a buckle, a tie, a clasp or any other available means to connect the device onto the patient P.

It should be noted that although a leg 42, joint 40 and leg 44 are depicted in the drawings that the goniometer may also be applied to other parts of the body. For example, an elbow joint about an upper or lower arm, a wrist about a lower arm and hand or an ankle about a lower leg and foot may also be effectively used with the device to measure the articulation of that joint.

Similarly, the device may also be applied to animals in a veterinary setting. Animals may also benefit from having the range of articulation determined by the device. With similar means and physical parts of the device, measurements can be derived on a wide variety of non-human animals.

The patient P may move the limbs about the joint 40 on their own power to show what they are innately able to perform. Alternatively, the healthcare provided may use this to manipulate the joint to determine the natural range of motion possible in the joint. Similarly, a healthcare provider may move the joint to determined the comfortable range of articulation of the joint for pain measurements as reported by the patient P or a determined by alternate pain determinative means used in the clinical setting.

A hinge 18 connects the arm 14 and arm 16. The hinge 18 is generally placed against the joint 40 of the patient P being measured. With the arm 14 aligned with the bone in the leg 42 and the arm 16 aligned along the bone in the leg 44, the device parallels the movement of the patient P during articulation of that joint 40.

For example, if the relative angle between the leg 42 and leg 44 at the joint 40 is a given value, then the angle between the arm 14 and arm 16 about the hinge 18 will be the same. During use, as the joint 40 articulates, equally the hinge 18 will articulate. When the device is connected to the patient P the angle between the arm 14 and 16 is generally the same as between the leg 42 and 44. As noted above, the term leg is exemplary of anatomical parts that could equally be other body parts about a joint, whether human or animal.

In some cases the precise angle between the arms 14 and 16 may not exactly match the angle between the legs 42 and 44. In other words, the arms 14 and 16 may not exactly parallel the long bones on either side of the joint 40. The important concept is that they are linearly relatively consistent to determine a change in range from one measurement session to another so that changes in range of motion may be observed and recorded to determine the progress of the patient P.

For example, if when positioned on the patient the device indicates a measured range of motion from ten to forty degrees, thus determining a net thirty degrees of motion. This does not necessarily indicate that the precise angles between the long bones in the leg 42 and 44 are exactly at ten through forty degrees. This does mean that the legs 42 and 44 articulated a net thirty degree range.

It is important that the arm 16 be placed along the bone in the leg 44 and the arm 14 be placed along the bone in leg 42 precisely the same relative way each time the device is applied to the patient P from measuring session to session.

To achieve consistency between measurement sessions the goniometer must be placed on a specific patient in the precise same manner each time a measurement is taken of the range of motion of that joint 40. This is done on the first use by placing the device onto the patient's body over the joint 40 to be measured for a first baseline measurement. The arm 14 is placed onto the leg 42 and the straps 20 and 21 are tightened against the leg 42 by closures 32 and 33. Similarly, the arm 16 is placed against the leg 44 and the strap 22 is closed with closure 34 to hold the device against the patient's P leg. A mark 36 is made on the leg 44 corresponding to the notch 26 on the arm 16 and a mark 38 is made on the leg 42 corresponding to the notch 24 on the arm 14.

On any subsequent time the device is attached to the patient P the notch 24 is aligned with mark 38 prior to affixing the arm 14 to the leg 42 with the straps 20 and 21 and the notch 26 is aligned with mark 36 before affixing the arm 26 to the leg 44 with the strap 22. In this way the arm 14 may consistently be affixed to the leg 42 with the same relation as arm 16 is affixed to the leg 44 from measurement session to measurement session with protracted times between sessions.

Figure 3:
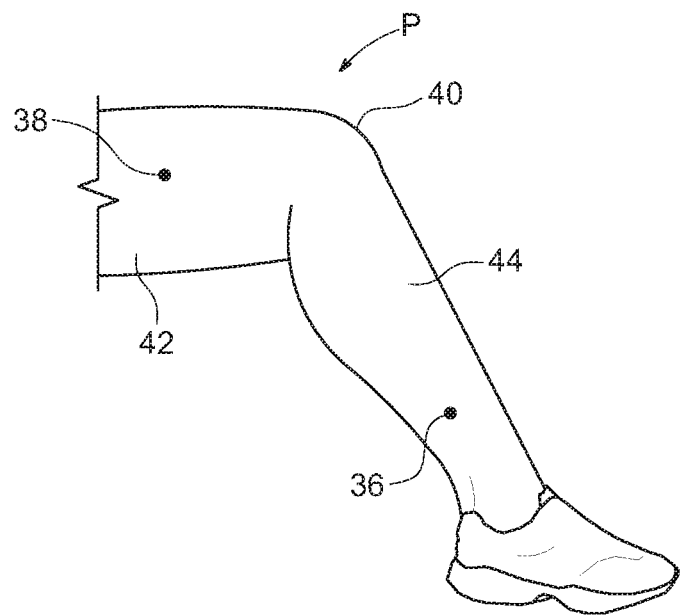
FIG. 3 shows an elevation view of a leg demonstrating examples of registration marks on the leg.
Figure 3A:
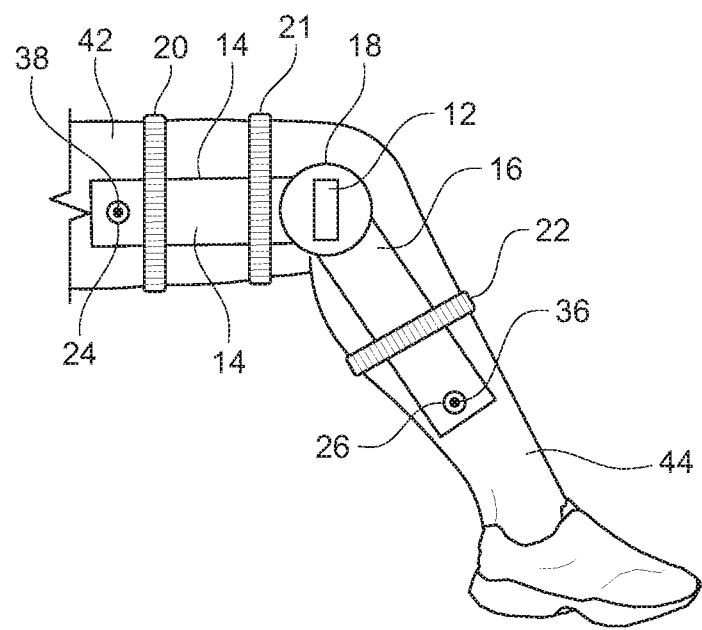
FIG. 3A shows an elevation view of a goniometer attached to a patient.

The mark 36 is shown in FIG. 3 as a spot on the leg 44 while mark 38 is shown as an alternative form of an indicator on the leg 42. The marks 36 and 38 may be anything that marks on the skin in a visible way an indicator of where to align the device onto the patient. The marks 36 and 38 could be a mark from an indelible ink, a tattoo, a stain or any other visible indicator on the skin that can be seen by the healthcare provider applying the goniometer to match up that mark with the notch 24 or 26 on the device.

It should be appreciated that mark 36 could be any reasonable shape or design that ensures consistent location of the goniometer on the legs 42 and 44. Again, the term legs is intended to be any body parts on either side of a human or animal joint. For example, the marks 36 and 38 could be a dot, an arrow, a bracket or any other indicator of the type that would allow repeatable affixing of each arm 14 and 16 onto the legs 42 and 44 in the same location on different occasions.

The notches 24 and 26 are shown in the drawings to be notched cutouts on the arms 14 and 16, respectively. The notches 24 and 26 should be appreciated to be any registration indicator that is on the arms 14 and 16 to be used to match up to the marks on the limbs on either side of the joint being measured. Equally effective, the notches 24 and 26 could be another type or form of marking on or connected to the arms 14 and 16.

For example, a line, a dimple on the arms, a slot, a mark, a sight window or any other feature that could be used by the healthcare provider to line up the arms 14 and 16 with a registration mark 36 and 38 on the body parts of the patient P whose joint range is being evaluated could be alternatively provided within the inventive scope of the device. The mark 36 shown in FIG. 1 is as viewed through the clothing and is not applied to the clothing because the clothing would move or be changed from session to session.

A version of the inventive concept can be fairly described as a joint measuring device comprised of, among other features, a first beam and a second beam. The first beam at a first end is affixed to a hinge. The second beam a first end is affixed to the hinge. The first beam articulates relative to the second beam about the hinge to approximately match the angles of the body part being measured. The first beam has a first strap that selectively attaches the first beam to a first predetermined limb for example with a buckle. The second beam has a second strap that selectively attaches the second beam a second predetermined limb similarly to the first. The first limb and second limb are connected by an articulating joint, such as a knee. A digital display is integral to the joint measuring device so that it can be viewed by the administrating healthcare provider to measure the joint angle. The digital display shows a value comprised of a relative angle between the first beam and the second beam in real time thus approximating the angle of the bones about the joint. The first beam on a second end has a first registration indicator such as a notch. The second beam on a second end has a second registration indicator such as a notch. A wireless signal comprised of the value is broadcast by the joint measuring device to a remote device is optionally present.

The inventive concept can also be fairly described as a method of measuring a joint articulation range of motion comprised of first providing any version of the joint measuring device as described above and then positioning the hinge adjacent to the articulating joint. Then securing both the first strap to the first preselected limb and the second strap to the second preselected limb. Next, applying a first index mark to the first predetermined limb adjacent to the first registration indicator. Also, applying a second index mark to the second predetermined limb adjacent to the second registration indicator. Then articulating the first predetermined limb relative to the second predetermined limb to a first position and recording a first value. Then articulating the first predetermined limb relative to the second predetermined limb to a second position and recording a second value. Then, calculating a third value from the difference between the first value and the second value wherein the third value is a range of joint articulation. Optionally, then finally comparing the third value determined at a first point in time to the third value at a second point in time to include as a factor in determining a course of medical treatment.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A joint measuring device comprised of a first beam and a second beam;
   the first beam at a first end is affixed to a hinge;
   the second beam at a first end is affixed to the hinge;
   the first beam articulates relative to the second beam about the hinge;
   the first beam has a first strap that selectively attaches the first beam to a first predetermined limb;
   the second beam has a second strap that selectively attaches the second beam at a second predetermined limb;
   the first limb and second limb are connected by an articulating joint;
   a digital display is integral to the joint measuring device;
   the digital display shows a value comprised of a relative angle between the first beam and the second beam in real time;
   the first beam on a second end has a first registration indicator;
   the second beam on a second end has a second registration indicator;
   a first index mark that corresponds to the first registration indicator is configured to be applied to the first predetermined limb when the first strap is secured to the first predetermined limb;
   a second index mark that corresponds to the second registration indicator is configured to be applied to the second predetermined limb when the second strap is secured to the second predetermined limb;
   a wireless signal comprised of the value is broadcast by the joint measuring device to a remote device.

2. A method of measuring a joint articulation range of motion comprised of:
   providing the joint measuring device of claim 1;
   positioning the hinge adjacent to the articulating joint;
   securing both the first strap to the first preselected limb and the second strap to the second preselected limb;
   applying the first index mark to the first predetermined limb adjacent to the first registration indicator;
   applying the second index mark to the second predetermined limb adjacent to the second registration indicator;
   articulating the first predetermined limb relative to the second predetermined limb to a first position and recording a first value;
   articulating the first predetermined limb relative to the second predetermined limb to a second position and recording a second value;
   calculating a third value from the difference between the first value and the second value wherein the third value is a range of joint articulation.

3. The method of claim 2 further comprising comparing the third value determined at a first point in time to a third value at a second point in time to include as a factor in determining a course of medical treatment.

* * * * *